(12) United States Patent
Labash

(10) Patent No.: US 8,137,379 B2
(45) Date of Patent: Mar. 20, 2012

(54) PRESSURE-APPLYING DEVICE

(76) Inventor: Josiah Labash, Port Hueneme, CA (US)

( * ) Notice: Subject to any disclaimer, the term of this patent is extended or adjusted under 35 U.S.C. 154(b) by 201 days.

(21) Appl. No.: 12/799,806

(22) Filed: May 3, 2010

(65) Prior Publication Data
US 2011/0270013 A1 Nov. 3, 2011

(51) Int. Cl.
*A61B 17/00* (2006.01)
(52) U.S. Cl. .................. 606/204; 269/3; 269/6; 29/268
(58) Field of Classification Search .......... 606/201, 606/202, 203, 204, 204.15, 204.25, 205–208; 81/98, 99, 111, 328, 321, 385, 389, 390, 81/394, 395, 399, 421, 422, 423, 424; 269/3, 269/6, 95; 29/268, 276, 278
See application file for complete search history.

(56) References Cited

U.S. PATENT DOCUMENTS

| | | | |
|---|---|---|---|
| 2,197,128 A * | 4/1940 | Harrison | 81/314 |
| 2,531,285 A * | 11/1950 | Manspeaker | 81/344 |
| 3,220,241 A * | 11/1965 | Miller | 72/446 |
| 3,456,262 A * | 7/1969 | Coon | 24/501 |
| 3,514,731 A | 5/1970 | Drake | |
| 3,577,583 A | 5/1971 | Amann | |
| 3,582,609 A | 6/1971 | Morley et al. | |
| 3,742,957 A * | 7/1973 | White | 606/208 |
| 3,981,209 A * | 9/1976 | Caroff | 81/367 |
| 4,013,932 A | 3/1977 | Aggarwal | |
| 4,549,536 A * | 10/1985 | Varjabedian | 601/135 |
| 5,094,227 A * | 3/1992 | Eglauf et al. | 601/135 |
| 5,113,727 A * | 5/1992 | Foster | 81/423 |
| 5,284,487 A * | 2/1994 | Hartmeister | 606/205 |
| 5,465,500 A | 11/1995 | Nammoto | |
| 5,584,854 A * | 12/1996 | Minarik | 606/201 |
| 5,609,317 A | 3/1997 | Glynn et al. | |
| 5,709,647 A * | 1/1998 | Ferber | 601/134 |
| 6,026,716 A * | 2/2000 | Orlosky | 81/360 |
| 6,227,081 B1 * | 5/2001 | Bally et al. | 81/389 |
| 6,240,815 B1 * | 6/2001 | Huang | 81/328 |
| 6,241,693 B1 * | 6/2001 | Lambden | 601/15 |
| 6,283,766 B1 | 9/2001 | Donnelly et al. | |
| 6,311,586 B1 * | 11/2001 | Hirse | 81/99 |
| 6,336,386 B1 * | 1/2002 | Lee | 81/328 |
| 6,502,482 B1 * | 1/2003 | Putsch et al. | 81/405 |
| 6,564,703 B1 * | 5/2003 | Lin | 100/234 |
| 6,656,199 B1 | 12/2003 | Lafontaine | |
| D487,930 S * | 3/2004 | Amoroso | D24/200 |
| 6,711,789 B2 * | 3/2004 | Ping | 24/505 |
| 6,765,465 B2 | 7/2004 | Dunning et al. | |
| 6,973,859 B2 * | 12/2005 | Noniewicz | 81/320 |

(Continued)

*Primary Examiner* — Gary Jackson
*Assistant Examiner* — Katrina Stransky
(74) *Attorney, Agent, or Firm* — Albert O. Cota

(57) ABSTRACT

A pressure-applying device (PAD) (10) that is attached to a selected location on a person's skin for therapeutic purposes. The PAD (10) comprises a first handle (12) having an articulated arm (38) with a tip (40) and a second handle (66) having an integral arm (92) with a tip (94). The first handle (12) is swively attached to the second handle (66) at a spring-loaded pivot point that allows the device (10) to be pressure-attached to the skin. A magnetic or non-magnetic sphere (132) is attached to each respective tip (40,94). When the PAD (10) is attached to a person's skin the sphere is pressure-interfaced on the skin. A tension screw (46) interfaces with the two handles (12,66) and allows the PAD (10) to apply adjustable pressure. The locations on person's skin where the PAD (10) is attached are designated according to traditional acupressure techniques.

9 Claims, 4 Drawing Sheets

U.S. PATENT DOCUMENTS 7,077,855 B2 * 7/2006 Curtis ........................... 606/204
2002/0151930 A1 * 10/2002 Mills ........................... 606/204
2003/0195558 A1 * 10/2003 Curtis ........................... 606/201
2004/0003687 A1 * 1/2004 An ........................... 81/427

* cited by examiner

PRESSURE-APPLYING DEVICE

TECHNICAL FIELD

The invention generally pertains to therapeutic products, and more particularly to a pressure-applying device that is attached to a selected location on a person's skin for a therapeutic purpose such as acupressure.

BACKGROUND ART

Holistic and/or non-western health practices have become widely used alternatives to conventional health/medical methodology. Many of the holistic/non-western practices utilize natural organic medicines and/or ancient techniques such as acupuncture, acupressure and magnetic therapy. Although the actual medical benefit(s) of acupuncture, acupressure or magnetic therapy have not been proven by western scientists/ doctors, many people claim significant improvement in a medical condition as a result of these methods. Whether the improvement is actual or psychological does not matter to the proponents as long as they experience the benefits. As a result, many westerners are willing to try one or more of these methods, especially when other conventional methods have not been successful.

As its name implies, acupuncture consists of inserting a multiplicity of small, thin needles into a person's skin at certain locations on the body. There are more than one thousand pre-mapped locations on the human body and the locations are chosen based on whatever ailment or condition a person is experiencing. By inserting the needles, a person's chi, or life-force, can be manipulated.

Acupressure is based on the same principle of acupuncture but is non-invasive. Instead of inserting needles, a person will have pressure applied at certain locations on their skin/body. A significant benefit to the practice of acupressure and other similar pressure-applied therapies, is a device that can be quickly and easily attached or removed from a person's skin. By utilizing a multiplicity of these devices, the time required for an acupressure session can be greatly reduced. Also, these devices are cleaner and allow greater control over the amount of pressure that is applied.

Magnetic therapy is an alternative medicine practice involving the use of static magnetic fields. Practitioners claim that subjecting certain parts of the body to magnetostatic fields produced by permanent magnets has beneficial health effects. These benefits may be specific, as in the case of wound healing, or more general, as for increased energy and vitality. An improvement would be to include magnetic therapy to the acupressure technique. If there was a device available that could provide both the benefits of pressure along with magnetism the use of such a device could potentially help many people.

A search of the prior art did not disclose literature or patents that read directly on the claims of the instant invention. However, the following U.S. patents are considered related.

| PATENT NO. | INVENTOR | ISSUED |
| --- | --- | --- |
| 3,577,583 | Amann | 4 May 1971 |
| 6,656,199 | LaFontaine | 2 Dec. 2003 |

The U.S. Pat. No. 3,577,583 discloses a clamp for releasably holding sheet material. The clamp includes a rigid base of nonmagnetic material and an elongated strip of flexible material. The base carries a permanent magnet at one end, and the elongated strip is attached to the other end of the base and carries a second permanent magnet overlying the permanent magnet in the base.

The U.S. Pat. No. 6,656,199 discloses a magnetic clamp assembly for an elongated flexible medical device. The clamp assembly includes magnetic clamp members operably coupled to clamp a portion of the flexible medical device to secure the medical device during treatment.

For background purposes and as indicative of the art to which the invention relates, reference may be made to the following remaining patents found in the search.

| PATENT NO. | INVENTOR | ISSUED |
| --- | --- | --- |
| 3,514,731 | Drake | 26 May 1970 |
| 3,582,609 | Morley | 1 Jun. 1971 |
| 4,013,932 | Aggarwal | 22 Mar. 1977 |
| 5,465,500 | Nammoto | 4 Nov. 1995 |
| 5,609,317 | Glynn et al | 11 Mar. 1997 |
| 6,283,766 | Donnelly et al | 4 Sept. 2001 |
| 6,765,465 | Dunning et al | 20 Jul. 2004 |

DISCLOSURE OF THE INVENTION

The pressure-applying device (PAD), which is also known as, is designed to be attached at a selected location on a person's skin for therapeutic purposes. The number of PADs that are attached ranges from 1-50, and the duration of time that the PADs are attached on the skin ranges from 30 seconds-60 minutes.

In its most basic design, the PAD is comprised of a first handle having an articulated arm with an inner surface, an outer surface and a tip, and a second handle having an integral arm with an inner surface, an outer surface and a tip. The first handle is swively attached to the second handle at a spring-loaded pivot point, and the pressure that is applied is adjustable by means of a tension screw that interfaces with the two handles.

Located at the inner surface of the tips on the two arms is a cavity and placed partially within the cavity and attached to the inner surface of each tip is a sphere. Each sphere is made of plastic, metal or wood and can further comprise a magnet. When a magnet is utilized the PAD provides both the therapeutic effect of pressure as well as magnetism on a person's skin. Typically, the locations on a person's skin where the PAD is attached are designated according to traditional acupressure techniques.

In view of the above disclosure, the primary object of the invention to provide a pressure-applying device that provides the therapeutic effect of pressure, with or without magnetism, at selected locations on a person's skin.

In addition to the primary object of the invention, it is also an object of the invention to provide a pressure-applying device that:

is convenient and easy to use,
 can reduce the time required for an acupressure session,
 can be easily stored and transported,
 can be color-coded for placement at various locations on a person's skin/body,
 requires no maintenance,
 can be sold as an acupressure kit consisting of multiple PADs along with varying-strength magnetic and nonmagnetic replaceable spheres, can be used on adults or children, and is cost effective from both a manufacturer's and consumer's point of view.

These and other objects and advantages of the present invention will become apparent from the subsequent detailed description of the preferred embodiment and the appended claims taken in conjunction with the accompanying drawings.

BEST MODE FOR CARRYING OUT THE INVENTION

Figure 1:
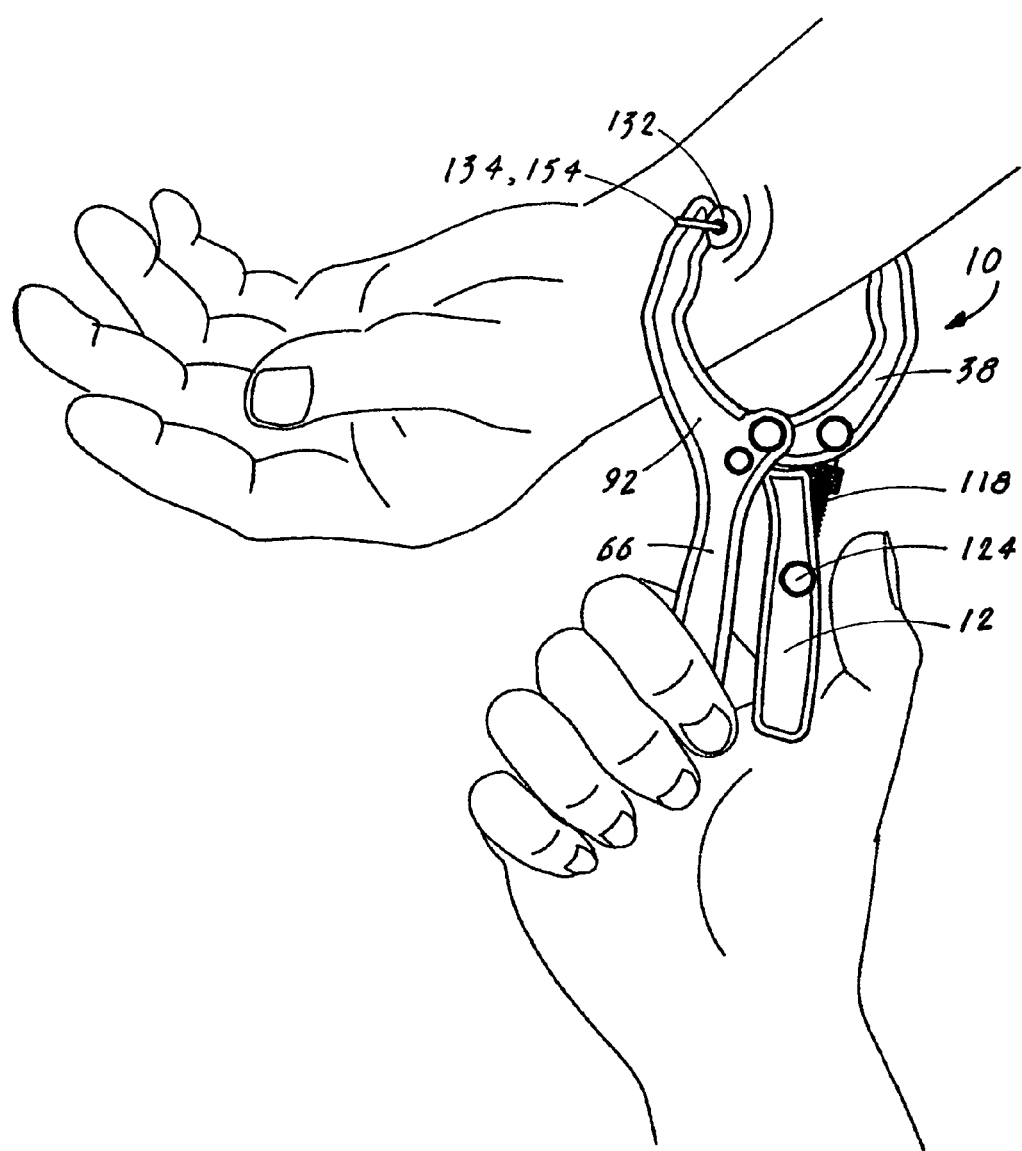
FIG. 1 is a perspective view of a pressure-applying device (PAD) attached to a selected location on a person's skin

The best mode for carrying out the invention is presented in terms that disclose a preferred embodiment of a pressure-applying device 10 ("PAD 10"). As described herein and shown assembled in FIG. 1, and an exploded view in FIG. 7, the PAD 10 is designed to be attached to a selected location on a person's skin. The PAD 10 provides the therapeutic effects of pressure on the skin. The locations on a person's skin where the PAD 10 is attached are typically chosen according to traditional acupressure techniques.

Figure 5:
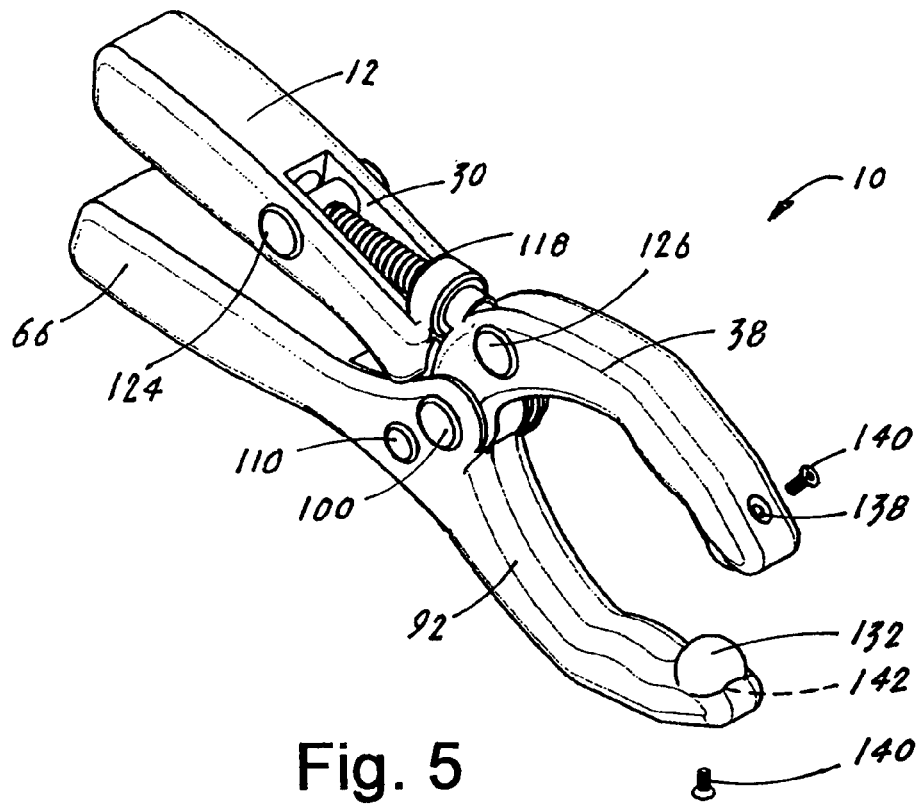
FIG. 5 is a perspective view of the PAD with a sphere attached by means of a screw that is first inserted through a bore in the PADs tip and then into a cavity in the sphere.
Figure 6:
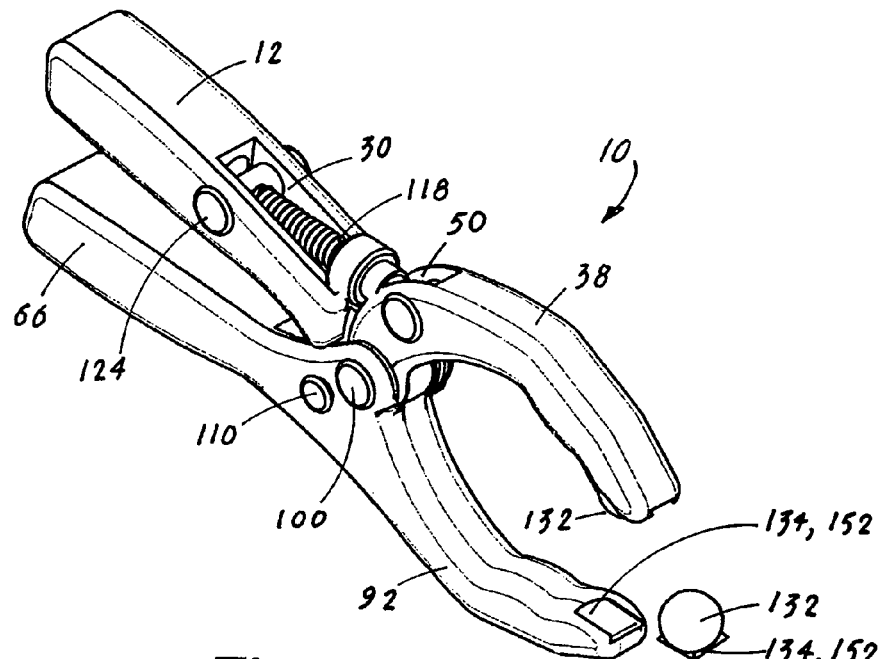
FIG. 6 is a perspective view of the PAD with a sphere attached by means of an adhesive.
Figure 7:
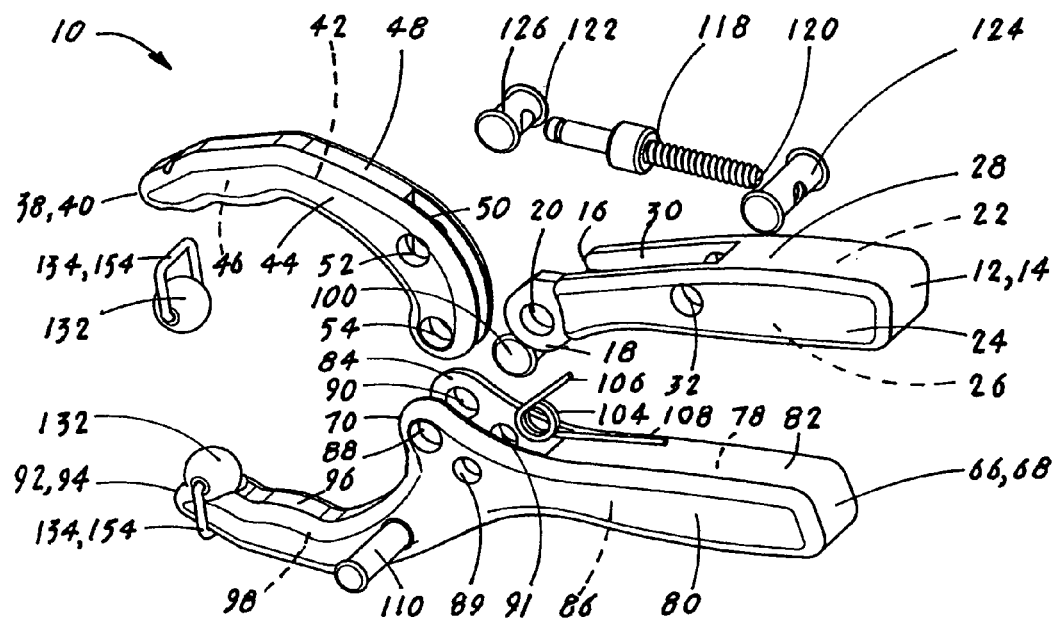
FIG. 7 is an exploded view of the PAD.

As shown in FIGS. 1-7, the PAD 10 is comprised of a first handle 12 and a second handle 66. The two handles 12,66 are made of a material that is selected from the group consisting of plastic, metal or wood. As best shown in FIG. 7, the first handle 12 has a rear end 14, a front end 16, a front tab 18 with a tab bore 20, a first side surface 22, a second side surface 24, an inner surface 26, an outer surface 28 with a handle slot 30, and a bore 32. Longitudinally extending from the first handle 12 is an articulated arm 38 which has a tip 40, a first side surface 42, a second side surface 44, an inner surface 46, an outer surface 48 with an arm slot 50, a first arm bore 52 and a second arm bore 54. The articulated arm 38 is swively attached to the first handle 12 by inserting the front tab 18 into the arm slot 50.

The second handle 66 has a rear end 68, a front end 70, a first side surface 78, a second side surface 80, an inner surface 82 with a slot 84, an outer surface 86, a third bore 90, a fourth bore 91, a first bore 88, a second bore 89, and an integral arm 92 having a tip 94, an inner surface 96, and an outer surface 98. The PAD 10 is assembled by placing the first handle's front tab 18 with the articulated arm 38 into the slot 84 on the second handle 66. Then, sequentially insert a pivot pin 100 through the first bore 88 on the second handle 66, the second bore 54 on the articulated arm 38 the tab bore 20 on the front tab 18, and the third bore 90 on the second handle 66.

Located and held by a spring pin 110 wherein the slot 84 on the second handle 66 is a spring 104 having an upper arm 106 and a lower arm 108. As shown in FIG. 7, the upper arm 106 interfaces with the first handle 12, and the lower arm 108 interfaces with the second handle 66.

In order to adjust the amount of pressure that the PAD 10 applies on a person's skin, a tension screw 118 is utilized. As shown in FIG. 7, the tension screw 118 has a first end 120, a second end 122, a first attachment pin 124 that is inserted into the bore 32 on the first handle 12, and a second attachment pin 126 that is inserted into the first bore 52 on the articulated arm 38.

Figure 2:
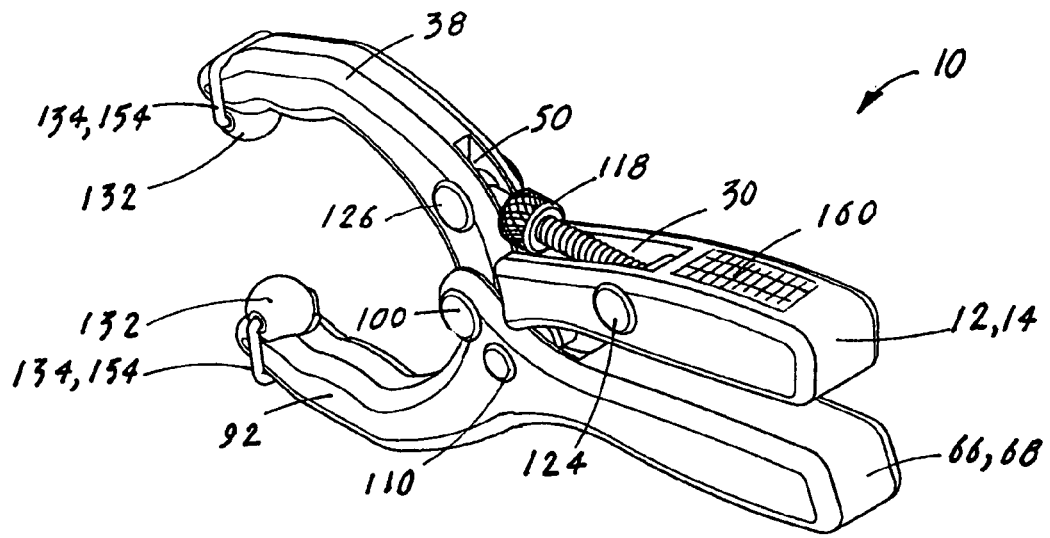
FIG. 2 is a perspective view of the PAD with a sphere attached by means of a clip and a handle having a textured surface.
Figure 3:
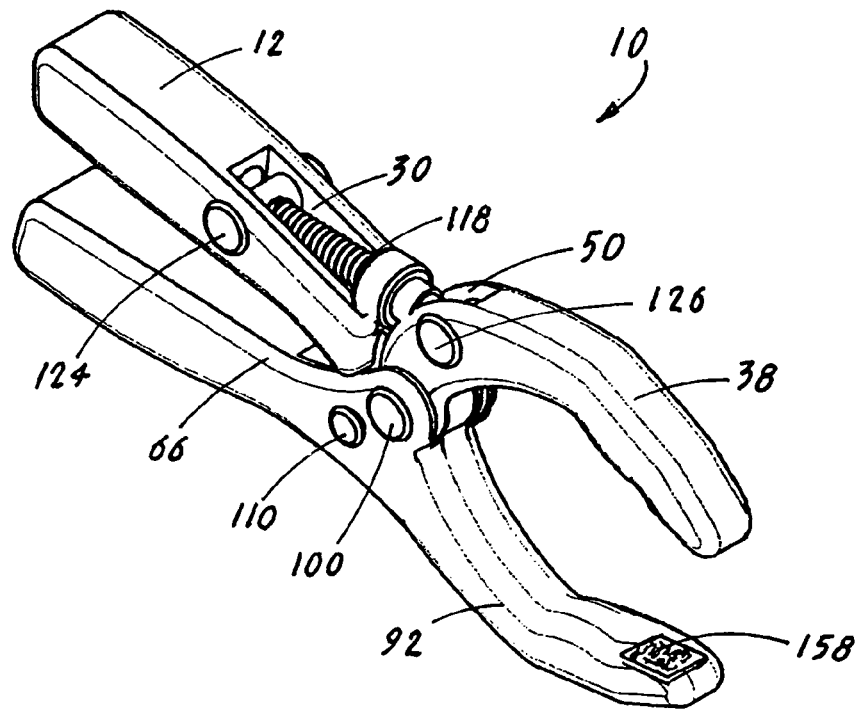
FIG. 3 is a perspective view of the PAD without a sphere.
Figure 4:
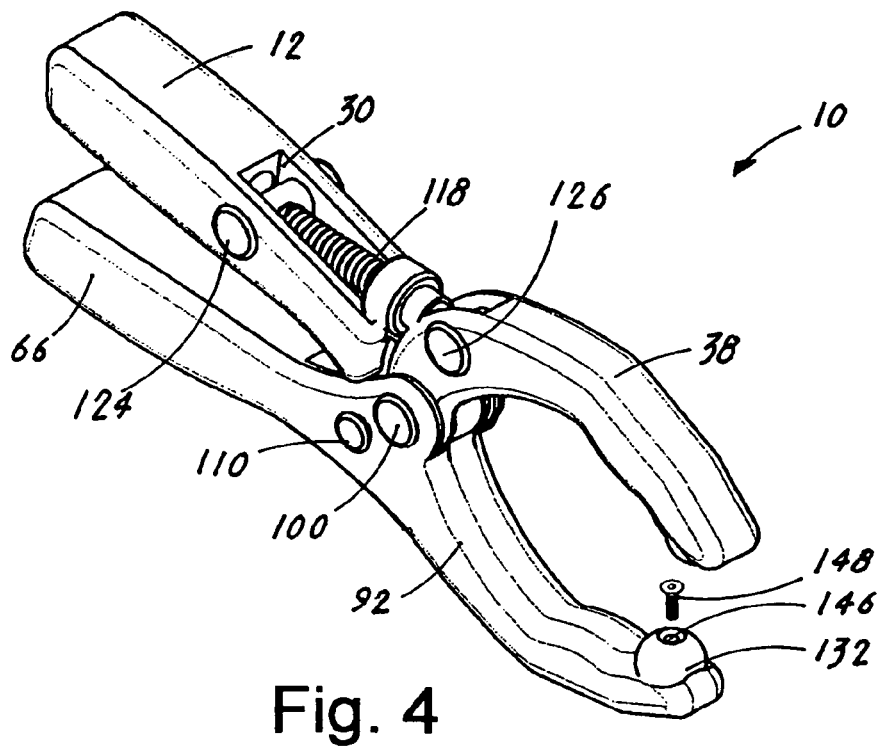
FIG. 4 is a perspective view of the PAD with a sphere attached by means of a screw that is first inserted through a bore in the sphere and then into a cavity in the PADs tip.

As shown in FIGS. 2, 4-6, a sphere 132 is attached by an attachment means 134 to each respective tip 40,94. A PAD 10 without a sphere 132 is shown in FIG. 3. When the PAD 10 is attached to a person's skin the sphere 132 will be pressure-interfaced on the skin. While a sphere shape is preferred, other geometric shapes such as a square with flat surfaces can also be utilized. The attachment means 134 can utilize several methods. The first attachment method, as shown in FIG. 4, is comprised of the sphere 132 having a bore 146 therethrough into which is inserted a screw 148 or bolt which then extends into the inner surface 46 or 96 of the tip 40 or 94. The second attachment method, as shown in FIG. 5, is comprised of a bore 138 that extends through the tip 40 or 94 and a screw 140 that is inserted through the bore 138 and into a cavity 142 which extends into the sphere 132. The third attachment method, as shown in FIG. 6, is comprised of an adhesive 152, and the fourth attachment method, as shown in FIG. 2, is comprised of a clip 154.

The sphere 132 is made of a material that is selected from the group consisting of plastic, metal or wood. Preferably the sphere 132 is comprised of a magnet which allows the PAD 10, when attached to a person's skin, to provide the therapeutic effects of magnetism. The magnetic sphere 132 can further be removed and replaced by another magnetic sphere 132 having either a weaker or stronger magnetic strength. The types of magnets that can be utilized include ceramic, alnico and rare earth magnets.

As shown in FIG. 2, the PAD 10 can further comprise a gripping surface 158 that covers the sphere 132 and provides a secure attachment of the PAD 10 to a person's skin. Additionally, the first handle 12 and second handle 66 can have a textured surface 160 that provides a secure grip for a person who is attaching the PAD 10.

To use the PAD 10 the following steps are performed:

1. Select a location on a person's skin. The locations are typically designated according to traditional acupressure techniques.

2. Grasp the PAD 10, adjust the tension screw 118 to a desired pressure, and apply inward pressure to the pair of handles 12,66 which causes the two arms 38,92 to open.

3. Place the PAD 10 at the selected location with a small amount of skin between the tips 40,94 of the arms 38,92.

4. Release the inward pressure, thereby causing the arms 38,92 to close with the tips 40,94 pinching the skin therebetween.

5. Repeat steps 1-4 at other selected locations on a person's skin by utilizing multiple PADs 10, and 6. After a selected duration of time re-apply inward pressure to each respective pair of handles 12,66 which allows all the attached PADs 10 to be removed from the person's skin.

While the invention has been described in detail and pictorially shown in the accompanying drawings it is not to be limited to such details, since many changes and modifications may be made to the invention without departing from the spirit and the scope thereof. Hence, it is described to cover any and all modifications and forms which may come within the language and scope of the claims.

The invention claimed is:

1. A pressure-applying device that is attached to a selected location on a person's skin for therapeutic purposes, wherein the locations on a person's skin where said device is attached are designated according to traditional acupressure techniques, wherein said device is comprised of:
   a) a first handle having a rear end, a front end, a front tab having a tab bore, a first side surface, a second side surface, an inner surface, an outer surface having a handle slot, and a bore,
   b) an articulated arm having a tip, a first side surface, a second side surface, an inner surface, an outer surface with an arm slot, a first arm bore and a second arm bore, wherein said articulated arm is swively attached to said first handle by inserting the front tab into the arm slot,
   c) a second handle having a rear end, a front end, a first side surface, a second side surface, an inner surface having a slot, an outer surface, a first bore, a second bore, a third bore, a fourth bore and an integral arm having a tip, an inner surface and an outer surface, wherein said device is assembled by placing said first handle's front tab with said articulated arm into the slot on said second handle and then sequentially inserting a pivot pin through the first bore on said second handle, the second bore on said articulated arm, the tab bore on the front tab, and the third bore on said second handle,
   d) a spring having an upper arm and a lower arm, wherein said spring is located and held by a spring pin within the slot on said second handle, wherein the upper arm of said spring interfaces with the first handle and the lower arm interfaces with the second handle,
   e) a tension screw having a first end, a second end, a first attachment pin that is inserted into the bore on said first handle, and a second attachment pin that is inserted into the first bore on said articulated arm, wherein said tension screw allows said device to apply adjustable pressure on a person's skin, and
   f) a sphere that is attached by an attachment means to a cavity located on each respective tip, wherein when said device is attached to a person's skin said sphere is pressure-interfaced on the skin.

2. The pressure-applying device as specified in claim 1 wherein said sphere is made of a material that is selected from the group consisting of plastic, metal and wood.

3. The pressure-applying device as specified in claim 1 wherein said sphere is a magnet.

4. The pressure-applying device as specified in claim 1 where the attachment means for attaching said sphere to the tip is comprised of said sphere having a bore therethrough into which is inserted a screw or bolt which then extends into the inner surface of the tip.

5. The pressure-applying device as specified in claim 1 wherein the attachment means for attaching said sphere to the tip is comprised of a bore that extends through the tip on the elongated arm and a screw that is inserted through the bore and into a cavity which extends into said sphere.

6. The pressure-applying device as specified in claim 1 wherein the attachment means for attaching said sphere to the tip is comprised of an adhesive.

7. The pressure-applying device as specified in claim 1 wherein the attachment means for attaching said sphere to the tip is comprised of a clip.

8. The pressure-applying device as specified in claim 1 wherein said sphere further comprising a textured surface that provides a secure attachment of said device to the skin.

9. A method for attaching a pressure-applying device according to claim 1 to a person's skin, wherein said method comprises the following steps:
   a) select a location on a person's skin wherein typically the locations are designated according to traditional acupressure techniques,
   b) grasp said device, adjust a tension screw to a desired pressure, and apply inward pressure to a pair of handles which causes a pair of elongated arms to open,
   c) place said device at the selected location with a portion of skin between the tips of the elongated arms,
   d) release the inward pressure, thereby causing the elongated arms to close with the tips pinching the skin,
   e) repeat steps a)-d) at other selected locations on a person's skin by utilizing multiple devices, wherein the number of devices that are attached to selected locations on a person's skin ranges from 1 to 50, wherein the duration of time that said devices are attached ranges from 30 seconds to 60 minutes, and
   f) after the selected duration of time, re-apply inward pressure to each respective pair of handles which allows said devices to be removed from the skin.

* * * * *